(12) United States Patent
Parisotto et al.

(10) Patent No.: US 10,842,926 B2
(45) Date of Patent: Nov. 24, 2020

(54) MEDICAL FLUID TREATMENT MACHINES AND RELATED SYSTEMS AND METHODS

(71) Applicant: Fresenius Medical Care Deutschland GmbH, Bad Homburg (DE)

(72) Inventors: Maria Teresa Parisotto, Bad Homburg (DE); Francesco Pelliccia, Giorgio a Cremano (IT); Cristina Miriunis, Bad Homburg (DE); Stefano Stuard, Francavilla al Mare (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 256 days.

(21) Appl. No.: 14/596,361

(22) Filed: Jan. 14, 2015

(65) Prior Publication Data

US 2016/0199562 A1    Jul. 14, 2016

(51) Int. Cl.
*A61M 1/36* (2006.01)
*A61M 1/16* (2006.01)
(Continued)

(52) U.S. Cl.
CPC ........ *A61M 1/3607* (2014.02); *A61M 1/1603* (2014.02); *A61M 1/28* (2013.01); *A61M 1/3403* (2014.02); *G06F 19/3481* (2013.01); *G16H 50/30* (2018.01); *A61B 5/02225* (2013.01); *A61B 5/4839* (2013.01); *A61M 1/341* (2014.02); *A61M 2205/3303* (2013.01); *A61M 2205/3331* (2013.01); *A61M 2205/3344* (2013.01); *A61M 2205/3375* (2013.01); *A61M 2205/3379* (2013.01); *A61M 2205/3576* (2013.01); *A61M 2205/50* (2013.01); *A61M 2205/502* (2013.01); *A61M 2205/505* (2013.01); *A61M 2205/52* (2013.01); *A61M 2205/84* (2013.01); *A61M 2230/005* (2013.01); *A61M 2230/04* (2013.01);
(Continued)

(58) Field of Classification Search
CPC .......... A61M 2230/05; A61M 2230/20; A61M 2230/005; A61M 2205/52; A61M 2205/502; A61M 2205/3303; G16H 50/30
See application file for complete search history.

(56) References Cited

U.S. PATENT DOCUMENTS 4,967,754 A    11/1990  Rossi
5,842,996 A *  12/1998  Gruenfeld .......... A61B 5/02233
                                                                600/490
(Continued)

FOREIGN PATENT DOCUMENTS

CN    101611409    12/2009
CN    101853330    10/2010
(Continued)

OTHER PUBLICATIONS

US 8,510,132 B2, 08/2013, Seward (withdrawn)
(Continued)

*Primary Examiner* — Leslie R Deak
(74) *Attorney, Agent, or Firm* — Fish & Richardson P.C.

(57) ABSTRACT

A method comprising: receiving patient assessment information concerning one or more subjective characteristics of a patient; determining a patient assessment score based on the received patient assessment information; and modifying operation of a medical fluid treatment machine based on the patient assessment score.

16 Claims, 22 Drawing Sheets

(51) Int. Cl.
*A61M 1/28* (2006.01)
*A61M 1/34* (2006.01)
*G16H 50/30* (2018.01)
*G06F 19/00* (2018.01)
*A61B 5/00* (2006.01)
*A61B 5/022* (2006.01)

(52) U.S. Cl.
CPC ..... *A61M 2230/20* (2013.01); *A61M 2230/30* (2013.01); *A61M 2230/40* (2013.01); *A61M 2230/63* (2013.01)

(56) References Cited

U.S. PATENT DOCUMENTS

| | | | |
|---|---|---|---|
| 5,860,932 A * | 1/1999 | Goto | A61B 5/02116 600/485 |
| 7,788,038 B2 | 8/2010 | Oshita et al. | |
| 7,890,341 B2 | 2/2011 | McNally et al. | |
| 8,092,380 B2 | 1/2012 | Rothman et al. | |
| 8,100,829 B2 * | 1/2012 | Rothman | G06Q 50/22 600/300 |
| 8,392,232 B2 | 3/2013 | McGillin | |
| 8,747,328 B2 * | 6/2014 | Tichauer | A61B 5/0225 600/485 |
| 8,769,625 B2 * | 7/2014 | Wang | G06F 19/3418 726/4 |
| 8,974,491 B2 * | 3/2015 | Leschinsky | A61B 5/02225 606/202 |
| 2006/0287906 A1 | 12/2006 | McGillin | |
| 2008/0154177 A1 * | 6/2008 | Moubayed | G06F 19/3468 604/19 |
| 2010/0010834 A1 | 1/2010 | Okon | |
| 2011/0105979 A1 * | 5/2011 | Schlaeper | A61B 5/0002 604/5.01 |
| 2012/0041771 A1 | 2/2012 | Cosentino et al. | |
| 2012/0154264 A1 | 6/2012 | Wang et al. | |
| 2013/0302841 A1 * | 11/2013 | Struck | G01N 33/6803 435/28 |
| 2014/0276549 A1 * | 9/2014 | Osorio | A61M 5/1723 604/503 |

FOREIGN PATENT DOCUMENTS

| | | |
|---|---|---|
| CN | 102159260 | 8/2011 |
| CN | 103402423 | 11/2013 |
| CN | 103717243 | 4/2014 |
| CN | 104217095 | 12/2014 |
| CN | 204016711 | 12/2014 |
| CN | 104582563 | 4/2015 |
| CN | 104834989 | 8/2015 |
| CN | 104850725 | 8/2015 |
| EP | 0911042 | 4/1999 |
| JP | 2003-47657 | 2/2003 |
| JP | 2014-4194 | 1/2014 |
| WO | WO9407210 A1 | 3/1994 |
| WO | WO 2008/064254 | 5/2008 |
| WO | WO 2010/028860 | 3/2010 |
| WO | WO 2013/101292 | 7/2013 |

OTHER PUBLICATIONS

Kevin Gunning & Kathy Rowan, ABC of Intensive Care, 319 Br. Med. J., 241-244, 243 (1999). (Year: 1999).*
Modified Barthel Index (Shah Version): Self Care Assessment.
Granger et al., "Stroke rehabilitation analysis of repeated Barthel Index measures", Archives of Physical and Medical Rehabilitation, 60, 14-17, (1979).
Hasselkus, B., "Barthel self-care index and geriatric home care patients", Physical and Occupational Therapy in Geriatrics, 1, 11-22, (1982).
Leonard et al., "The Barthel Index in an acute geriatric setting", American Journal of Occupational Therapy, 39, 41-43, (1992).
Shah et al., "Improving the sensitivity of the Barthel Index for stroke rehabilitation", Journal of Clinical Epidemiology, 42, 703-709, 1989.
Shah et al., "Documentation for measuring stroke rehabilitation outcomes", Australian Medical Records Journal, 21, 88-95, 1991.
Shah et al., "The Barthel Index and A D L evaluation in stroke rehabilitation in Australia, Japan, the UK and the USA", Australian Occupational Therapy Journal, 39, 5-13, 1992.
Fried, Linda et.al., "Charlson Comorbidity Index as a predictor of Outcomes in incident Peritoneal Dialysis Patients" Feb. 2001, 37(2):337-342.
Mansilla et al., "Impact of incident comorbidity on functional loss in elderly chronic kidney disease patients undergoing hemodialysis", CANNT Journal = Journal ACITN 22(1):25-29, Jan. 2012.

* cited by examiner

| AaCCI and Albumin Measurement | Probability of Survival (1 year) |
|---|---|
| AaCCI ≤ 3, albumin measurement < 3.5 g/dL | 87% |
| AaCCI = 4 or 5, albumin measurement < 3.5 g/dL | 61% |
| AaCCI = 6 or 7, albumin measurement < 3.5 g/dL | 49% |
| AaCCI ≥ 8, albumin measurement < 3.5 g/dL | 30% |
| AaCCI ≤ 3, albumin measurement ≥ 3.5 g/dL | 89% |
| AaCCI = 4 or 5, albumin measurement ≥ 3.5 g/dL | 75% |
| AaCCI = 6 or 7, albumin measurement ≥ 3.5 g/dL | 67% |
| AaCCI ≥ 8, albumin measurement ≥ 3.5 g/dL | 50% |

Fig. 7

| | | |
|---|---|---|
| *CHAIR/BED TRANSFERS* | 0 | Unable to participate in a transfer. Two attendants are required to transfer the patient with or without a mechanical device. |
| | 3 | Able to participate but maximum assistance of one other person is require in all aspects of the transfer. |
| | 8 | The transfer requires the assistance of one other person. Assistance may be required in any aspect of the transfer. |
| | 12 | The presence of another person is required either as a confidence measure, or to provide supervision for safety. |
| | 15 | The patient can safely approach the bed walking or in a wheelchair, lock brakes, lift footrests, or position walking aid, move safely to bed, lie down, come to a sitting position on the side of the bed, change the position of the wheelchair, transfer back into it safely and/or grasp aid and stand. The patient must be independent in all phases of this activity. |

Fig. 8a

| AMBULATION | 0 | Dependent in ambulation. |
| | 3 | Constant presence of one or more assistant is required during ambulation. |
| | 8 | Assistance is required with reaching aids and/or their manipulation. One person is required to offer assistance. |
| | 12 | The patient is independent in ambulation but unable to walk 50 metres without help, or supervision is needed for confidence or safety in hazardous situations. |
| | 15 | The patient must be able to wear braces if required, lock and unlock these braces assume standing position, sit down, and place the necessary aids into position for use. The patient must be able to crutches, canes, or a walkarette, and walk 50 metres without help or supervision. |

Fig. 8b

| | | |
|---|---|---|
| *AMBULATION/WHEELCHAIR* | | |
| * (If unable to walk) | 0 | Dependent in wheelchair ambulation. |
| Only use this item if the patient is rated "0" for Ambulation, and then only if the patient has been trained in wheelchair management. | 1 | Patient can propel self short distances on flat surface, but assistance is required for all other steps of wheelchair management. |
| | 3 | Presence of one person is necessary and constant assistance is required to manipulate chair to table, bed, etc. |
| | 4 | The patient can propel self for a reasonable duration over regularly encountered terrain. Minimal assistance may still be required in 'tight corners' or to negotiate a kerb 100mm high. |
| | 5 | To propel wheelchair independently, the patient must be able to go around corners, turn around, manoeuvre the chair to a table, bed, toilet, etc. The patient must be able to push a chair at least 50 metres and negotiate a kerb. |

Fig. 8c

| | | |
|---|---|---|
| STAIR CLIMBING | 0 | The patient is unable to climb stairs. |
| | 2 | Assistance is required in all aspects of stair climbing, including assistance with walking aids. |
| | 5 | The patient is able to ascend/descend but is unable to carry walking aids and needs supervision and assistance. |
| | 8 | Generally no assistance is required. At times supervision is required for safety due to morning stiffness, shortness of breath, etc. |
| | 10 | The patient is able to go up and down a flight of stairs safely without help or supervision. The patient is able to use hand rails, cane or crutches when needed and is able to carry these devices as he/she ascends or descends. |

Fig. 8d

| | | |
|---|---|---|
| TOILET TRANSFERS | 0 | Fully dependent in toileting. |
| | 2 | Assistance required in all aspects of toileting. |
| | 5 | Assistance may be required with management of clothing, transferring, or washing hands. |
| | 8 | Supervision may be required for safety with normal toilet. A commode may be used at night but assistance is required for emptying and cleaning. |
| | 10 | The patient is able to get on/off the toilet, fasten clothing and use toilet paper without help. If necessary, the patient may use a bed pan or commode or urinal at night, but must be able to empty it and clean it. |

Fig. 8e

| BOWEL CONTROL | | |
|---|---|---|
| | 0 | The patient is bowel incontinent. |
| | 2 | The patient needs help to assume appropriate position, and with bowel movement facilitatory techniques. |
| | 5 | The patient can assume appropriate position, but cannot use facilitatory techniques or clean self without assistance and has frequent accidents. Assistance is required with incontinence aids such as pad, etc. |
| | 8 | The patient may require supervision with the use of suppository or enema and has occasional accidents. |
| | 10 | The patient can control bowels and has no accidents, can use suppository, or take an enema when necessary. |

Fig. 8f

| BLADDER CONTROL | | |
|---|---|---|
| | 0 | The patient is dependent in bladder management, is incontinent, or has indwelling catheter. |
| | 2 | The patient is incontinent but is able to assist with the application of an internal or external device. |
| | 5 | The patient is generally dry by day, but not at night and needs some assistance with the devices. |
| | 8 | The patient is generally dry by day and night, but may have an occasional accident or need minimal assistance with internal or external devices. |
| | 10 | The patient is able to control bladder day and night, and/or is independent with internal or external devices. |

Fig. 8g

| | | |
|---|---|---|
| *BATHING* | 0 | Total dependence in bathing self. |
| | 1 | Assistance is required in all aspects of bathing, but patient is able to make some contribution. |
| | 3 | Assistance is required with either transfer to shower/bath or with washing or drying, including inability to complete a task because of condition or disease, etc. |
| | 4 | Supervision is required for safety in adjusting the water temperature, or in the transfer. |
| | 5 | The patient may use a bathtub, a shower, or take a complete sponge bath. The patient must be able to do all the steps of whichever method is employed without another person being present. |

Fig. 8h

| | | |
|---|---|---|
| *DRESSING* | 0 | The patient is dependent in all aspects of dressing and is unable to participate in the activity. |
| | 2 | The patient is able to participate to some degree, but is dependent in all aspects of dressing. |
| | 5 | Assistance is needed in putting on, and/or removing any clothing. |
| | 8 | Only minimal assistance is required with fastening clothing such as buttons, zips, bra, shoes, etc. |
| | 10 | The patient is able to put on, remove, corset, braces, as prescribed. |

Fig. 8i

| | | |
|---|---|---|
| PERSONAL HYGIENE (Grooming) | 0 | The patient is unable to attend to personal hygiene and is dependent in all aspects. |
| | 1 | Assistance is required in all steps of personal hygiene, but patient able to make some contribution. |
| | 3 | Some assistance is required in one or more steps of personal hygiene. |
| | 4 | Patient is able to conduct his/her own personal hygiene but requires minimal assistance before and/or after the operation. |
| | 5 | The patient can wash his/her hands and face, comb hair, clean teeth and shave. A male patient may use any kind of razor but must insert the blade, or plug in the razor without help, as well as retrieve it from the drawer or cabinet. A female patient must apply her own make-up, if used, but need not braid or style her hair. |

Fig. 8j

| | |
|---|---|
| FEEDING | 0 | Dependent in all aspects and needs to be fed, nasogastric needs to be administered |
| | 2 | Can manipulate an eating device, usually a spoon, but someone must provide active assistance during the meal. |
| | 5 | Able to feed self with supervision. Assistance is required with associated tasks such as putting milk/sugar into tea, salt, pepper, spreading butter, turning a plate or other "set up" activities. |
| | 8 | Independence in feeding with prepared tray, except may need meat cut, milk carton opened or jar lid etc. The presence of another person is not required. |
| | 10 | The patient can feed self from a tray or table when someone puts the food within reach. The patient must put on an assistive device if needed, cut food, and if desired use salt and pepper, spread butter, etc. |

Fig. 8k

| Score Range | Patient general condition classification |
|---|---|
| 4.3 to 5 | Fully complex patient |
| 3.5 to 4.2 | Substantially complex patient |
| 2.7 to 3.4 | Moderately complex patient |
| 1.9 to 2.6 | Minimally complex patient |
| 1 to 1.8 | Fully independent patient |

Fig. 10

| Patient Shift | |
|---|---|
| Patient | Combined Patient Assessment Score |
| 1 | 4.8 |
| 2 | 4.7 |
| 3 | 4.1 |
| 4 | 4.9 |
| 5 | 3.9 |
| 6 | 3.6 |
| 7 | 3.5 |
| 8 | 3.3 |
| 9 | 2.8 |
| 10 | 2.7 |
| 11 | 2.7 |
| 12 | 2.5 |
| 13 | 1.3 |
| 14 | 1.4 |
| 15 | 1.5 |
| 16 | 1.9 |
| Average | 3.1 |

| Nurse 1 | |
|---|---|
| Patient | Combined Patient Assessment Score |
| 1 | 4.8 |
| 7 | 3.5 |
| 11 | 2.7 |
| 13 | 1.3 |
| Average | 3.1 |

| Nurse 2 | |
|---|---|
| Patient | Combined Patient Assessment Score |
| 2 | 4.7 |
| 6 | 3.6 |
| 12 | 2.5 |
| 16 | 1.9 |
| Average | 3.2 |

| Nurse 3 | |
|---|---|
| Patient | Combined Patient Assessment Score |
| 3 | 4.1 |
| 5 | 3.9 |
| 9 | 2.8 |
| 14 | 1.4 |
| Average | 3.1 |

| Nurse 4 | |
|---|---|
| Patient | Combined Patient Assessment Score |
| 4 | 4.9 |
| 8 | 3.2 |
| 10 | 2.7 |
| 15 | 1.5 |
| Average | 3.1 |

Fig. 11

| Patient Shift | |
|---|---|
| Patient | General Patient Condition |
| 1 | 4,8 |
| 2 | 4,7 |
| 3 | 4,1 |
| 4 | 4,9 |
| 5 | 3,9 |
| 6 | 3,6 |
| 7 | 3,5 |
| 8 | 3,3 |
| 9 | 2,8 |
| 10 | 2,7 |
| 11 | 2,7 |
| 12 | 2,5 |
| 13 | 1,3 |
| 14 | 1,4 |
| 15 | 1,5 |
| 16 | 1,9 |
| Average | 3,1 |

| Experienced Nurse 1 | |
|---|---|
| Patient | General Patient Condition |
| 1 | 4,8 |
| 3 | 4,1 |
| 5 | 3,9 |
| Average | 4,3 |

| Experienced Nurse 2 | |
|---|---|
| Patient | General Patient Condition |
| 2 | 4,7 |
| 4 | 4,9 |
| 6 | 3,6 |
| Average | 4,4 |

| New Nurse 1 | |
|---|---|
| Patient | General Patient Condition |
| 7 | 3,5 |
| 10 | 2,7 |
| 12 | 2,5 |
| 14 | 1,4 |
| 15 | 1,5 |
| Average | 2,3 |

| New Nurse 2 | |
|---|---|
| Patient | General Patient Condition |
| 8 | 3,3 |
| 9 | 2,8 |
| 11 | 2,7 |
| 13 | 1,3 |
| 16 | 1,9 |
| Average | 2,4 |

Fig. 12

MEDICAL FLUID TREATMENT MACHINES AND RELATED SYSTEMS AND METHODS

TECHNICAL FIELD

This disclosure relates to medical fluid treatment machines and related systems and methods

BACKGROUND

During medical treatment of a patient, a medical device can monitor analytic characteristics of the patient to determine whether the treatment is effective. Certain adjustments can be made to the treatment to increase its effectiveness.

SUMMARY

In one aspect a method includes receiving patient assessment information concerning one or more subjective characteristics of a patient. The method also includes determining a patient assessment score based on the received patient assessment information. The method also includes modifying operation of a medical fluid treatment machine based on the patient assessment score.

Implementations can include one or more of the following features.

In some implementations, modifying operation of the medical fluid treatment machine includes adjusting a treatment parameter of the medical fluid treatment machine.

In some implementations, treatment parameters of the medical fluid treatment machine include blood flow rate, ultrafiltration rate, blood pressure monitoring rate, and vascular access monitoring.

In some implementations, modifying operation of the medical fluid treatment machine includes causing a message to be displayed that suggests an adjustment of a treatment parameter of the medical fluid treatment machine.

In some implementations, the method also includes receiving an input in response to the message. The method also includes upon receiving the input, adjusting the treatment parameter according to the suggestion.

In some implementations, the patient assessment information includes a probability of the patient surviving for a particular length of time. The patient assessment information also includes information related to self-care and mobility of the patient. The patient assessment information also includes information related to needs, preferences, and abilities of the patient.

In some implementations, the information related to the needs, preferences, and abilities of the patient includes information related to gastro-intestinal symptoms, respiratory distress, pain, mobility, chronic interdialytic muscle cramps, skin color and integrity, oedema, vascular access, and changes in mental state.

In some implementations, the information related to the self-care or mobility of the patient includes information related to chair or bed transfer ability, ambulation dependency, wheelchair dependency, stair climbing ability, toilet transfer ability, bowel control, bladder control, bathing ability, dressing ability, personal hygiene maintenance ability, and feeding ability.

In some implementations, the probability of the patient surviving for a particular length of time is based on an Age adjusted Charlson Comorbidity Index and a concentration of albumin in the blood of the patient.

In some implementations, the method also includes assigning a particular caregiver to the patient based on the patient assessment score.

In some implementations, the patient assessment information and the patient assessment score are used in a data mining application.

In some implementations, the medical fluid treatment machine is a blood treatment machine.

In some implementations, the medical fluid treatment machine is a dialysis machine.

In some implementations, the dialysis machine is a hemodialysis machine.

In some implementations, the dialysis machine is a peritoneal dialysis machine.

In some implementations, the patient assessment information is received from a caregiver.

In another aspect, a medical fluid treatment machine includes a pump configured to pump medical fluid to and from a patient. The medical fluid treatment machine also includes an input device configured to receive patient assessment information concerning one or more subjective characteristics of the patient. The medical fluid treatment machine also includes a control unit that is in communication with the pump and the input device. The control unit configured to determine a patient assessment score based on the patient assessment information. The control unit is also configured to modify operation of the medical fluid treatment machine based on the patient assessment score.

Implementations can include one or more of the following features.

In some implementations, modifying operation of the medical fluid treatment machine includes adjusting a treatment parameter of the medical fluid treatment machine.

In some implementations, treatment parameters of the medical fluid treatment machine include blood flow rate, ultrafiltration rate, blood pressure monitoring rate, and vascular access monitoring.

In some implementations, the medical fluid treatment machine also includes a display. Modifying operation of the medical fluid treatment machine includes displaying a message on the display that suggests an adjustment of a treatment parameter of the medical fluid treatment machine.

In some implementations, the input device is also configured to receive an input in response to the message. The control unit is also configured to adjust the treatment parameter according to the suggestion upon receiving the input.

In some implementations, the patient assessment information includes a probability of the patient surviving for a particular length of time. The patient assessment information also includes information related to self-care and mobility of the patient. The patient assessment information also includes information related to needs, preferences, and abilities of the patient.

In some implementations, the information related to the needs, preferences, and abilities of the patient includes information related to gastro-intestinal symptoms, respiratory distress, pain, mobility, chronic interdialytic muscle cramps, skin color and integrity, oedema, vascular access, and changes in mental state.

In some implementations, the information related to the self-care or mobility of the patient includes information related to chair or bed transfer ability, ambulation dependency, wheelchair dependency, stair climbing ability, toilet transfer ability, bowel control, bladder control, bathing ability, dressing ability, personal hygiene maintenance ability, and feeding ability.

In some implementations, the probability of the patient surviving for a particular length of time is based on an Age adjusted Charlson Comorbidity Index and a concentration of albumin in the blood of the patient.

In some implementations, the medical fluid treatment machine is a blood treatment machine.

In some implementations, the medical fluid treatment machine is a dialysis machine.

In some implementations, the dialysis machine is a hemodialysis machine.

In some implementations, the dialysis machine is a peritoneal dialysis machine.

In some implementations, the medical fluid is blood.

In some implementations, the medical fluid is dialysate.

In another aspect, a computer-readable storage medium stores a computer program. The computer program includes instructions for causing a computer to receive patient assessment information concerning one or more subjective characteristics of a patient. The computer program also includes instructions for causing the computer to determine a patient assessment score based on the received patient assessment information. The computer program also includes instructions for causing the computer to modify operation of a medical fluid treatment machine based on the patient assessment score.

In another aspect, a system includes multiple medical fluid treatment machines. Each medical fluid treatment machine includes a pump configured to pump medical fluid to and from a patient associated with the medical fluid treatment machine. Each medical fluid treatment machine also includes an input device configured to receive patient assessment information concerning one or more subjective characteristics of the patient. Each medical fluid treatment machine also includes a control unit that is in communication with the pump and the input device. The control unit is configured to determine a patient assessment score based on the patient assessment information. The control unit is also configured to modify operation of the medical fluid treatment machine based on the patient assessment score. The system also includes a central server in communication with the medical fluid treatment machines. The central server is configured to receive the patient assessment scores and the patient assessment information from the medical fluid treatment machines. The central server is also configured to assign a particular caregiver to a particular patient based on the patient assessment score of the particular patient.

Implementations can include one or more of the following features.

In some implementations, the central server is also configured to analyze historical data related to patient assessment information and patient assessment scores. The central server is also configured to identify a treatment trends that corresponds to particular patient assessment information and a particular patient assessment score. The central server is also configured to propose implementing a treatment modification that, if accepted, automatically modifies operation of medical fluid treatment machines that are associated with patients that have the particular patient assessment information and the particular patient assessment score.

In some implementations, the proposed treatment modification, if accepted, automatically modifies operation of medical fluid treatment machines that are associated with patients that have patient assessment information that is similar to the particular patient assessment information and a patient assessment score that is within a defined range of the particular patient assessment score.

Implementations can include one or more of the following advantages.

In some implementations, patient assessment information can be used to tailor the operating parameters of the dialysis machine to provide treatment that is especially personalized for the particular patient. The patient assessment information includes an Age adjusted Charlson Comorbidity Index (AaCCI) assessment that is adjusted based on an albumin measurement, a Nursing Patient Assessment, and a Modified Barthel Index assessment. Typically, a dialysis machine's operating parameters are based primarily on analytic medical parameters. However, some of the patient assessment information is based on subjective patient characteristics, such as the caregiver's personal assessment of the patient's symptoms, thereby giving the caregiver more discretion over the patient's treatment that would otherwise not be taken into account.

In some implementations, the patient assessment information can indicate the level of difficulty involved for a caregiver to treat a particular patient. Someone in charge of allocating resources in a treatment facility can consider the patients' patient assessment information when assigning particular patients to particular caregivers. Patients can be assigned such that the expected difficulty involved in dealing with their patients for each caregiver is evenly distributed. Alternatively, patients can be assigned such that experienced caregivers treat complex patients, and less experienced caregivers treat less complex patients.

In some implementations, historical data related to the patient assessment information can be used in data mining applications. The clinical server can evaluate and analyze volumes of historical data to detect treatment trends. Automated dialysis treatment can be refined over time based on statistical data.

Other aspects, features, and advantages of the invention will be apparent from the description and drawings, and from the claims.

DESCRIPTION OF DRAWINGS

FIG. 7 is a table showing the patient's probability of survival for one year based on the patient's AaCCI and albumin measurement for the AaCCI+albumin assessment of FIG. 6.

FIGS. 8a-8k show the items that are assessed for the Modified Barthel Index assessment of FIG. 6.

FIG. 10 is a table that illustrates a patient's general condition classification based on the Combined Patient Assessment Score determined using the method illustrated in FIG. 6.

FIGS. 11 and 12 are tables that illustrate possible resource allocation based on Combined Patient Assessment Scores of various patients.

DETAILED DESCRIPTION

In order to determine the appropriate care required for a dialysis patient, it is useful to assess the patient's characteristics at different intervals during treatment. Typically, analytical medical parameters are used to provide information for determining suitable operating parameters for the dialysis machine. However, analytical medical parameters often do not tell the whole story. For example, the patient may be experiencing large amounts of pain, or may have a difficult time taking care of himself or herself. Such subjective patient characteristics are relevant for determining suitable treatments for the patient, but they cannot be measured analytically.

Dialysis machine operating parameters can be tailored to provide treatment that is especially personalized for the particular patient. The patient typically undergoes three assessments: i) an Age adjusted Charlson Comorbidity Index (AaCCI) assessment that is adjusted based on an albumin measurement, ii) a Nursing Patient Assessment, and iii) a Modified Barthel Index assessment. These assessments can be performed at various times and at various frequencies, as described in more detail below. The patient receives a score for each of the three assessments, and the scores are used to ultimately determine a Combined Patient Assessment Score. The operating parameters of the dialysis machine can be tailored to the particular patient based on the patient's Combined Patient Assessment Score. Resources and workflows in a treatment center can also be allocated based on the patient's Combined Patient Assessment Score. Further, historical data related to the three patient assessments can be utilized in various data mining applications.

Figure 1:
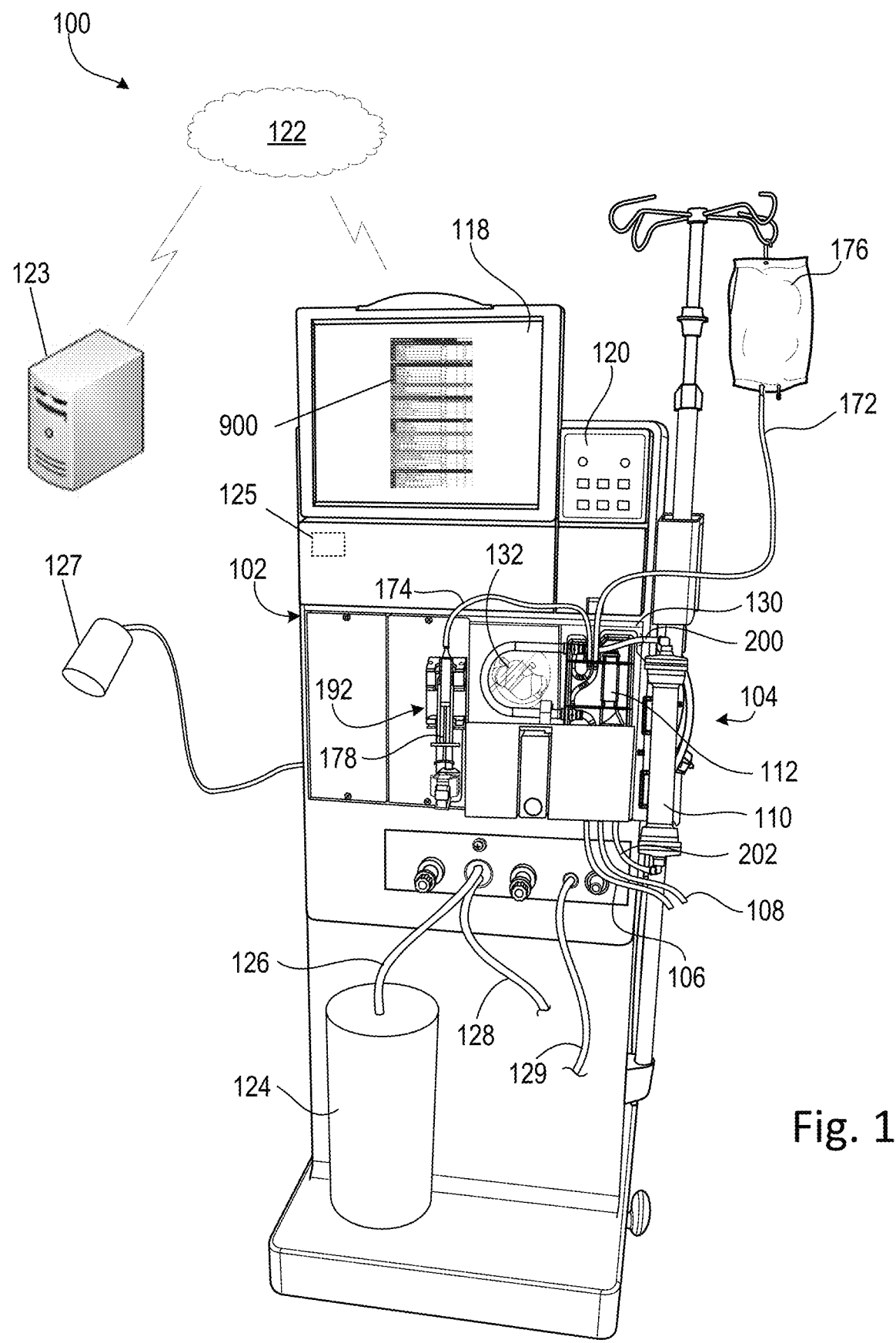
FIG. 1 is a front perspective view of a hemodialysis system that includes a hemodialysis machine in communication with a clinical server and a blood component set secured to the dialysis machine.

Referring to FIG. 1, a hemodialysis system 100 includes a hemodialysis machine 102. The hemodialysis machine 102 includes a touch screen 118 and a control panel 120. The touch screen 118 and the control panel 120 allow the operator to input various information to the hemodialysis machine 102 and to otherwise control the hemodialysis machine 102. In addition, the touch screen 118 serves as a display to convey information to the operator of the hemodialysis system 100.

The hemodialysis machine 102 includes a processor 125 that resides inside the machine that is connected to the touch screen 118 and the control panel 120. The processor 125 is configured to receive data that is input via the touch screen 118 and the control panel 120 and control the hemodialysis machine 102 based on the received data. For example, the processor 125 can adjust the operating parameters of the hemodialysis machine 102.

The hemodialysis machine 102 also includes a Blood Pressure Monitor (BPM) 127 for monitoring a blood pressure of a patient. The BPM 127 may be an automated, non-invasive blood pressure monitor that operates on the principle of oscillometry, such as a blood pressure cuff or sleeve. The BPM 127 may measure systolic blood pressure, diastolic blood pressure, mean arterial pressure (MAP), and information related to the pulse of the patient. While the BPM 127 shown in FIG. 1 is connected to the hemodialysis machine 102 by a wire, in some implementations, the BMP 127 is wirelessly connected to the hemodialysis machine 102 and is able to wirelessly communicate with the hemodialysis machine 102.

The hemodialysis machine 102 is connected to a network 122. The hemodialysis machine 102 is configured to communicate with a clinical server 123 via the network 122. The clinical server 123 can be accessible by many medical facilities of various types. In some implementations, the clinical server 123 is accessible by most or all medical facilities affiliated with a particular dialysis service provider. In certain implementations, the clinical server 123 is accessible by most or all medical facilities in a particular country or in multiple countries. The clinical server 123 is populated with data that is accessible by the hemodialysis machine 102, as explained in more detail below. The processor 125 is configured to receive data from the clinical server 123 and control the hemodialysis machine 102 based on the received data.

Information related to each of one or more assessments: i) the Age adjusted Charlson Comorbidity Index (AaCCI) assessment that is adjusted based on an albumin measurement, ii) the Nursing Patient assessment, and iii) the Modified Barthel Index assessment, can be input via the touch screen 118 or the control panel 120 and/or stored on the clinical server 123. The clinical server 123 is configured to access information that is input via the touch screen 118 and the control panel 120. The clinical server 123 analyzes the information related to each of the assessments for a particular patient and computes a Combined Patient Assessment Score. The operating parameters of the hemodialysis machine 102 are then tailored to the particular patient based on the Combined Patient Assessment Score.

The general operation of the hemodialysis machine 102 will now be described. Still referring to FIG. 1, a disposable blood component set 104 that forms a blood circuit is connected to the hemodialysis machine 102. During hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

One of the components of the blood component set 104 is an air release device 112. The air release device 112 includes a vent assembly 114 (shown in FIGS. 2, 3, and 5) that allows air to pass therethrough while inhibiting (e.g., preventing) liquid from passing therethrough. As a result, if blood passing through the blood circuit during treatment contains air, the air will be vented to atmosphere as the blood passes through the air release device 112.

As shown in FIG. 1, a dialysate container 124 is connected to the hemodialysis machine 102 via a dialysate supply line 126. A drain line 128 and an ultrafiltration line 129 also extend from the hemodialysis machine 102. The drain line 128 and ultrafiltration line 129 can be connected to a drain. The dialysate supply line 126, the drain line 128, and the ultrafiltration line 129 are fluidly connected to the various dialysate components and dialysate lines inside the housing of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 on the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130. As will be described in greater detail below, this arrangement facilitates control of the flow of blood through the blood circuit and monitoring of the blood flowing through the blood circuit.

Figure 2:
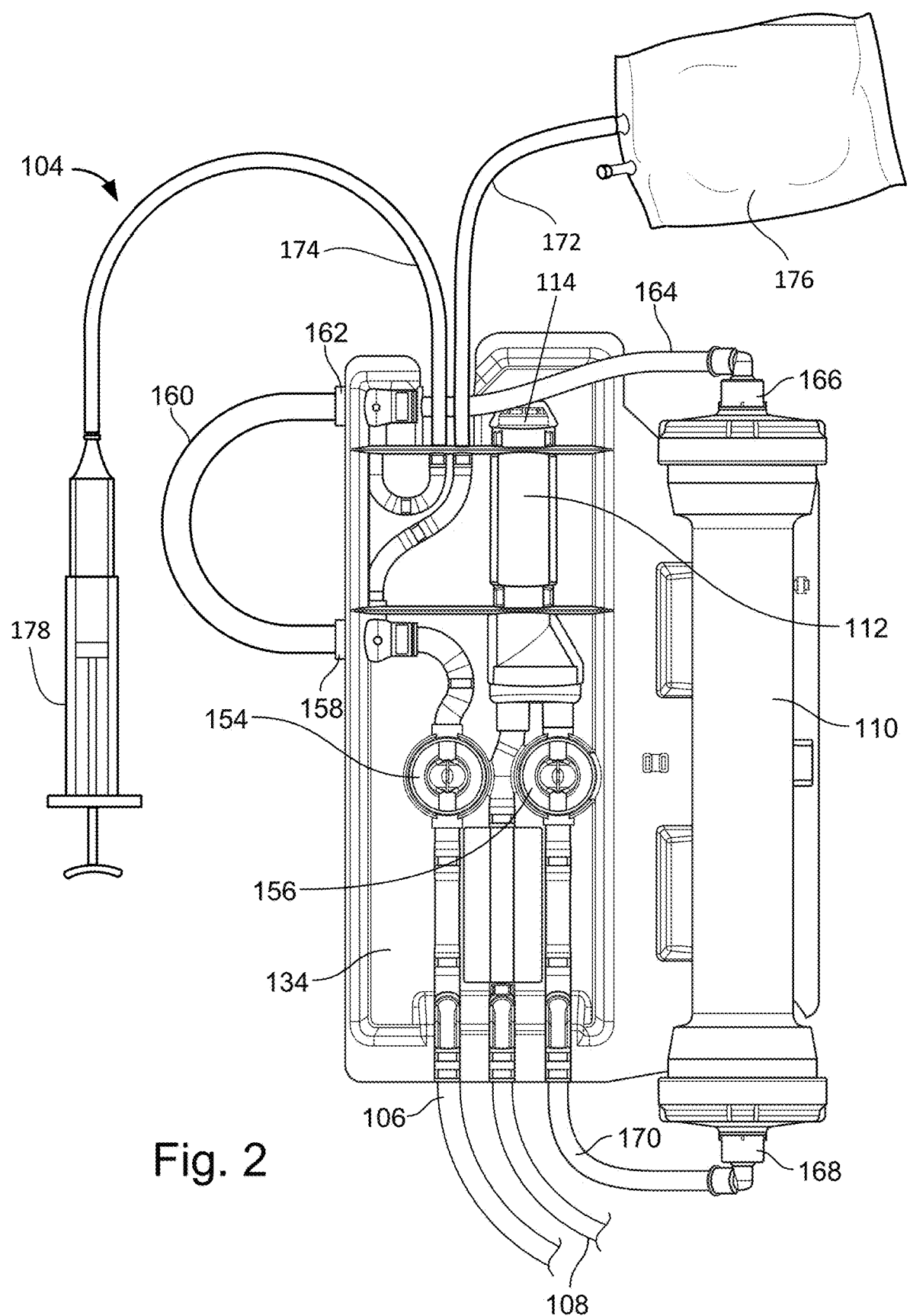
FIG. 2 is a front view of the blood component set of the hemodialysis system of FIG. 1.
Figure 3:
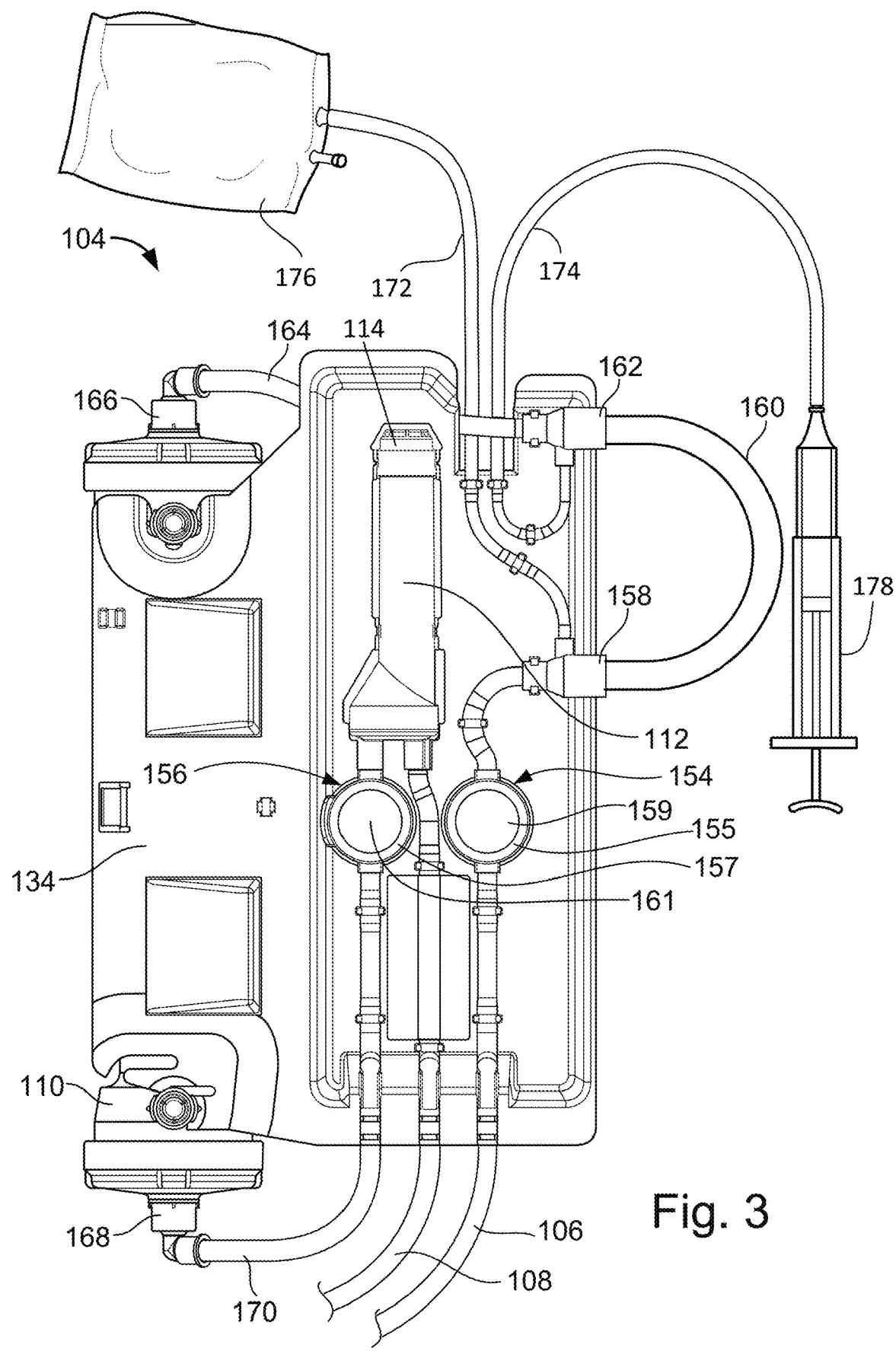
FIG. 3 is a rear view of the blood component set of the hemodialysis system of FIG. 1.

FIGS. 2 and 3 are front and back views, respectively, of the blood component set 104. As shown in FIGS. 2 and 3, the blood component set 104 includes various different blood lines and blood components, including the air release device 112, that are secured to a carrier body 134. The carrier body 134 forms a series of apertures and recesses for capturing and retaining the various blood lines and components. The carrier body 134 includes a recessed portion (shown on the left side of FIG. 2 and the right side of FIG. 3) and a flat portion (shown on the right side of FIG. 2 and the left side of FIG. 3). The recessed portion is configured to retain most of the blood components while the flat portion is configured to hold the dialyzer 110.

The air release device 112 is retained in an aperture formed in the carrier body 134. The air release device 112 can, for example, be snapped into the aperture formed in the carrier body 134. In some implementations, fingers extending from the carrier body 134 extend part way around the air release device 112 to retain the air release device 112 securely to the carrier body 134. The air release device 112, as noted above, allows gas, such as air, to escape from blood in the blood circuit and out of a chamber of the air release device 112 through the vent assembly 114 positioned at the top of the chamber.

Still referring to FIGS. 2 and 3, arterial and venous pressure sensor capsules 154, 156 are also positioned in apertures formed in the carrier body 134 of the blood component set 104. Each of the pressure sensor capsules 154, 156, as shown in FIG. 3, includes an annular rigid member 155, 157 to which a thin membrane 159, 161 is secured. The annular rigid members 155, 157 and the thin membranes 159, 161 of the capsules 154, 156 together form a pressure sensor chamber through which blood flows during use. When the blood component set 104 is secured to the front face of the module 130 of the hemodialysis machine 102, the thin membranes 159, 161 of the pressure sensor capsules 154, 156 face the front face of the module 130. The pressure within the pressure sensor chambers can be detected through the thin membranes 159, 161 by pressure sensors (e.g., pressure transducers) on the front face of the module 130 during use.

The arterial patient line 106, as shown in FIGS. 2 and 3, is contained within a recess formed in the carrier body 134. One end of the arterial patient line 106 is fluidly connected to an artery of a patient during treatment. The arterial patient line 106 is also fluidly connected to the pressure sensor capsule 154. The arterial patient line 106 extends along the recess to a first pump line adaptor 158, which connects the arterial patient line 106 to one end of a U-shaped pump line 160. The other end of the pump line 160 is connected to a second pump line adaptor 162, which is fluidly connected to a dialyzer inlet line 164. The dialyzer inlet line 164 is connected via a tube adaptor to a blood entry port 166 of the dialyzer 110. A blood exit port 168 of the dialyzer 110 is connected to another tube adaptor, which connects the dialyzer 110 to a dialyzer outlet line 170. The pressure sensor capsule 156 is positioned along the dialyzer outlet line 170, upstream of the air release device 112. The pressure sensor capsule 156 is fluidly connected to an entry port of the air release device 112. The pressure sensor capsule 156 allows blood pressure on the venous side of the dialyzer 110 to be sensed by a mating pressure sensor on the front face of the module 130 during treatment. The venous patient line 108 is connected to an exit port of the air release device 112. The venous patient line 108 extends from the air release device 112 and is fluidly connected to a vein of a patient during treatment.

Still referring to FIGS. 2 and 3, in addition to the blood lines forming the main blood circuit described above, a saline delivery line 172 and a drug delivery line 174 are connected to the blood circuit for introducing saline and drugs (e.g., heparin) into the blood circuit. The saline delivery line 172 is connected to a saline bag 176. The drug delivery line 174 is connected to a syringe 178 that contains a drug. The saline delivery line 172 is connected to the first pump line adaptor 158, and the drug delivery line 174 is connected to the second pump line adaptor 162. The various blood lines, the saline delivery line 172, and the drug delivery line 174 are typically retained within recessed channels formed in the carrier body 134.

Figure 4:
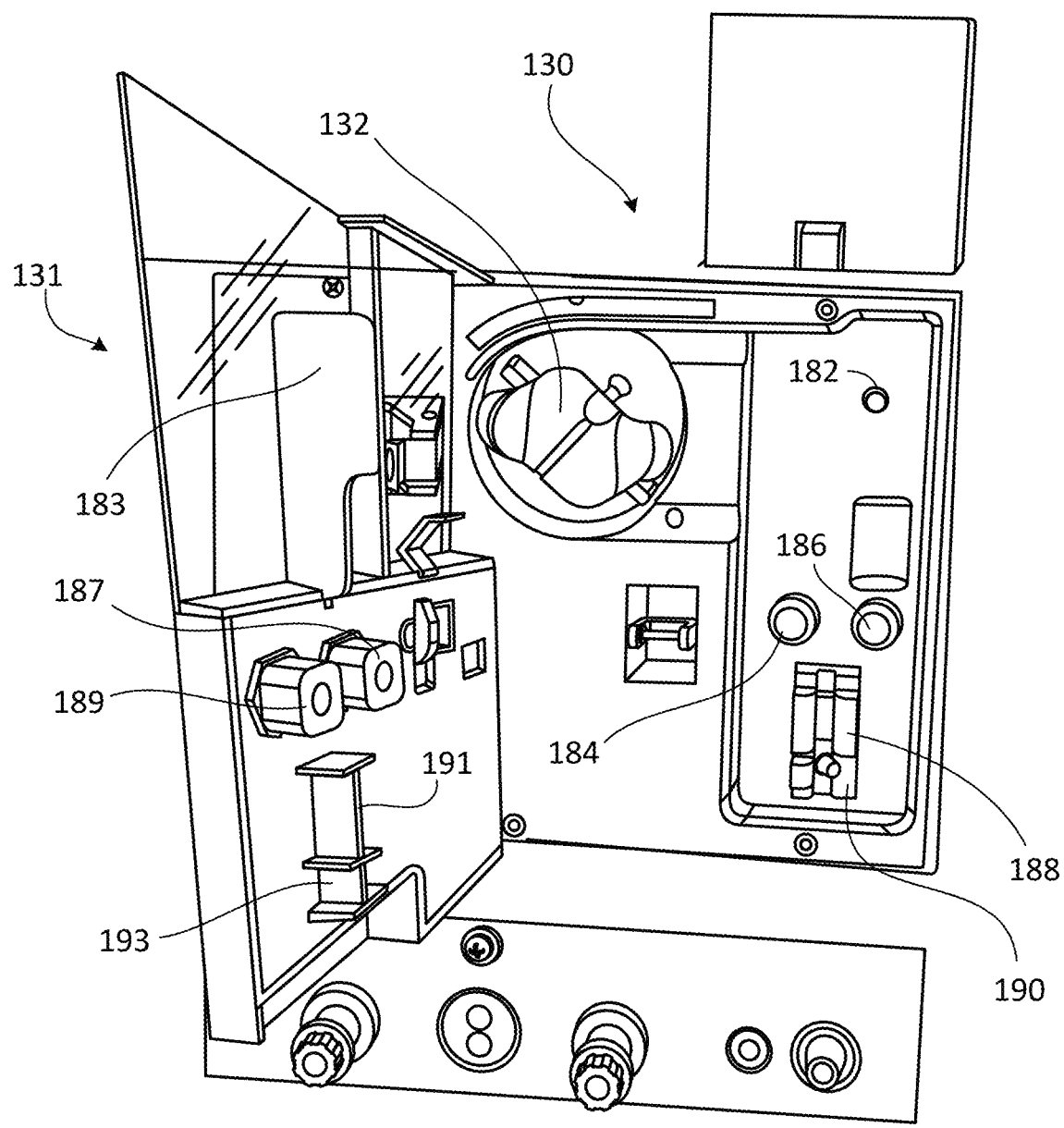
FIG. 4 is a front view of the hemodialysis machine of FIG. 1 with a door of the machine in an open position and with the blood component set removed from the machine to expose blood pumping and monitoring instruments on the front face of the machine.

FIG. 4 is an enlarged front view of the module 130 of the hemodialysis machine 102 with a door 131 of the module 130 open and the blood component set 104 removed from the module 130. The blood pump 132 extends from the front face of the module 130 of the hemodialysis machine 102. The blood pump 132 is a peristaltic pump and is arranged so that the U-shaped pump line 160 extending laterally from the carrier body 134 of the blood component set 104 is positioned around the peristaltic pump when the blood component set 104 is secured to the front face of the module 130.

The module 130 of the hemodialysis machine 102 also includes a level detector 182 that aligns with the air release device 112 when the blood component set 104 is secured to the front face of the module 130. The level detector 182 is adapted to detect the level of liquid (e.g., blood and/or saline) within the air release device 112. The door 131 of the module 130 includes a projection 183 that compresses the air release device 112 against the level detector 182 when the blood component set 104 is secured to the front face of the module 130 and the door 131 is closed. The projection 183 includes a recessed region adapted to receive the rounded exterior surface of the air release device 112. The recessed region helps to ensure that the air release device 112 is properly positioned with respect to the level detector 182 when the door 131 is closed. The level detector 182 is a cylindrical member having a relatively soft tip (e.g., a sponge tip) that contacts the outer surface of the air release device 112 when the door 131 presses the air release device 112 against the level detector 182. The tip of the level detector 182 includes an ultrasound signal transmitter and receiver for determining the level of liquid in the air release device 112. During use, the transmitter emits an ultrasonic signal that reflects off of the contents in the air release chamber. The reflected signal is then detected by the receiver. The reflected signal can be used to determine the contents in the air release chamber at the level of the level detector 182. The receiver can, for example, be adapted to distinguish between liquid, air, and a combination of liquid and air (e.g., foam). As a result, the level detector 182 can detect when the blood level within the chamber drops due to the entry of air into the chamber.

Still referring to FIG. 4, the module 130 of the hemodialysis machine 102 also includes arterial and venous pressure transducers 184, 186 that align with the pressure sensor capsules 154, 156 of the blood component set 104 when the blood component set 104 is secured to the front face of the module 130 and the door 131 of the module 130 is closed. The pressure transducers 184, 186 are capable of measuring the pressure of blood flowing through the capsules 154, 156. The pressure transducers 184, 186 are cylindrical members having substantially flat surfaces exposed on the front face of the module 130. The door 131 includes spring-loaded plungers 187, 189 that compress the annular rigid members 155, 157 (shown in FIG. 3) of the pressure sensor capsules 154, 156 between the door 131 and the front face of the module 130 when the blood component set 104 is secured to the front face of the module 130 and the door 131 is closed. As a result, the membranes 159, 161 (shown in FIG. 3) of the pressure sensor capsules 154, 156 are pressed against the pressure transducers 184, 186 and a seal is created between the perimeter of each of the thin membranes 159, 161 and the front face of the module 130. The central regions of the membranes 159, 161 of the pressure sensor capsules 154, 156 contact the flat surfaces of the pressure transducers 184, 186. As the fluid pressure changes within the pressure sensor capsules 154, 156, the amount of pressure applied to the pressure transducers 184, 186 by the pressure sensor capsules 154, 156 also changes. The pressure transducers 184, 186 are capable of detecting these pressure changes during use.

An air bubble detector 188 also extends from the front face of the module 130. When the blood component set 104 is secured to the front face of the module 130, the venous patient line 108 passes through (e.g., is threaded through) the air bubble detector 188. The air bubble detector 188 includes a housing that forms a channel in which the venous patient line 108 is received. The door 131 of the module 130 includes a fin 191 that presses the venous patient line 108 into the channel of the housing and against a sensor of the air bubble detector 188 when the door 131 is closed. The air bubble detector 188 is capable of detecting air bubbles within the venous patient line 108.

Downstream of the air bubble detector 188, the venous patient line 108 passes through (e.g., is threaded through) an occluder or clamp 190. Similar to the air bubble detector 188, the occluder 190 has a housing that forms a channel in which the venous patient line 108 is received. The door 131 of the module 130 includes a fin 193 that presses the venous patient line 108 into the channel of the housing of the occluder 190 when the door 131 is closed. The occluder 190 is configured to crimp the portion of the venous patient line 108 disposed therein to prevent blood from passing through the venous patient line 108 when activated. The occluder 190 can, for example, be connected to the air bubble detector 188 so that the occluder 190 can be activated when the air bubble detector 188 detects an air bubble within the venous patient line 108. Such an arrangement helps to ensure that no air bubbles reach the patient in the event that the air release device 112 fails to remove one or more air bubbles from the blood.

Referring briefly to FIG. 1, a drug pump 192 also extends from the front of the hemodialysis machine 102. The drug pump 192 is a syringe pump that includes a clamping mechanism configured to retain the syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via the drug delivery line 174 during use, or to draw liquid from the blood circuit into the syringe 178 via the drug delivery line 174 during use.

Still referring to FIG. 1, the dialysate circuit is formed by multiple dialysate components and dialysate lines positioned inside the housing of the hemodialysis machine 102 as well as the dialyzer 110, a dialyzer inlet line 200, and a dialyzer outlet line 202 that are positioned outside of the housing of the hemodialysis machine 102. The dialyzer inlet line 200 includes a connector adapted to connect to one end region of the dialyzer 110, and the dialyzer outlet line 202 includes a connector adapted to connect to another end region of the dialyzer 110.

Figure 5:
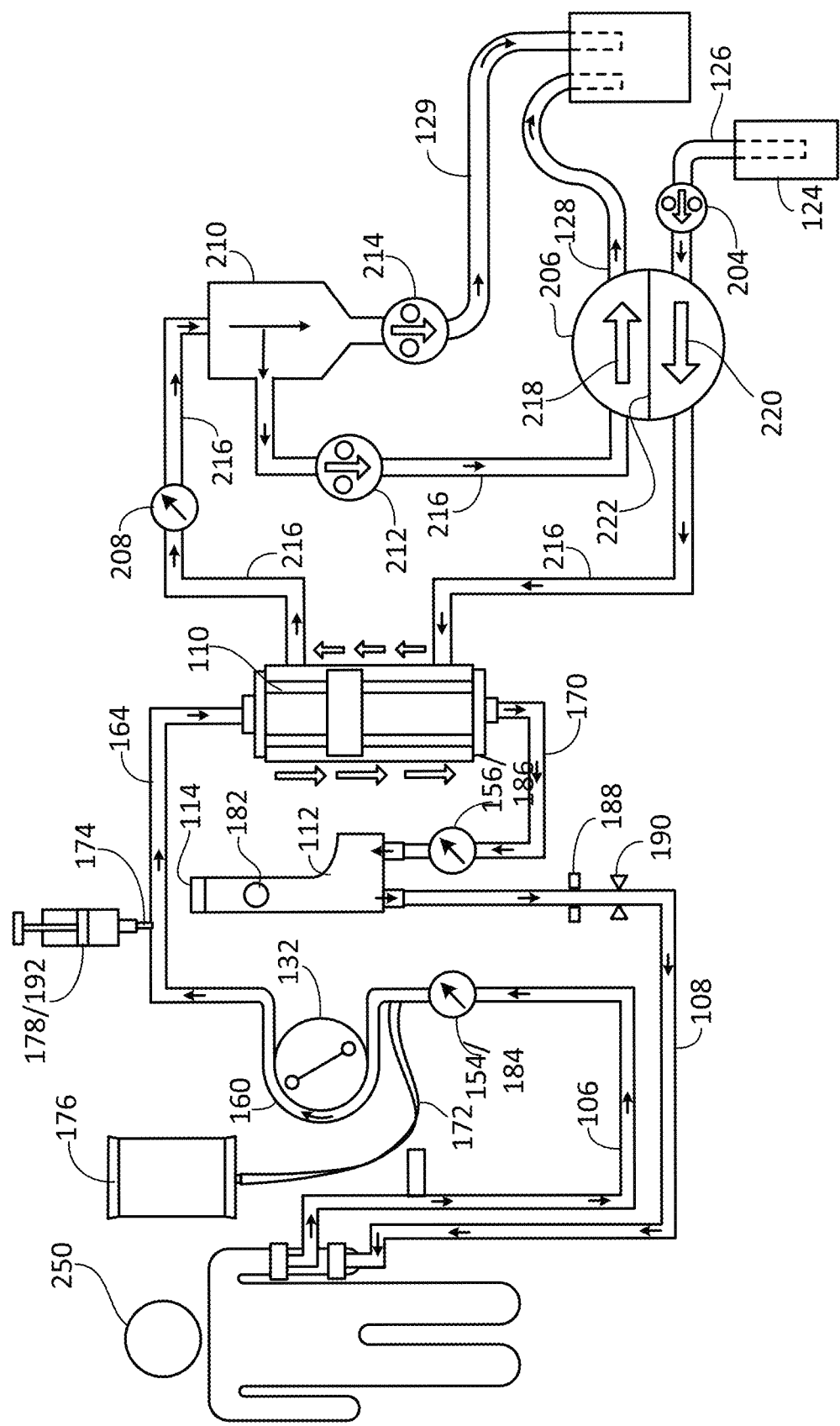
FIG. 5 is a schematic of fluid flow through a blood circuit and dialysate circuit of the hemodialysis system of FIG. 1 when the hemodialysis system is connected to a patient for treatment.

FIG. 5 is a schematic showing the flow paths of fluids into, through, and out of the blood circuit and the dialysate circuit of the hemodialysis system 100. Referring to the right side of FIG. 5, the dialysate components of the dialysate circuit that are located inside the housing of the hemodialysis machine 102 include a first dialysate pump 204, a balancing device 206, a pressure sensor 208, an equalizing chamber 210, a second dialysate pump 212, and an ultrafiltration pump 214. These dialysate components are fluidly connected to one another via a series of dialysate lines 216. The dialysate pump 204 is capable of pumping dialysate to the balancing chamber 206 from the dialysate container 124 via the dialysate supply line 126.

The balancing device 206 includes a spherical chamber that is divided into a first chamber half 218 and a second chamber half 220 by a flexible membrane 222. As fluid flows into the first chamber half 218, fluid is forced out of the second chamber half 220, and vice versa. This balancing device construction helps to ensure that the volume of fluid entering the balancing device 206 is equal to the volume of fluid exiting the balancing device 206. This helps to ensure that the volume of fresh dialysate entering the dialysate circuit is equal to the volume of spent dialysate exiting the dialysate circuit when desired during treatment, as described in greater detail below.

During hemodialysis, the dialysate exiting the second chamber half 220 is directed through the dialyzer 110 toward the equalizing chamber 210. The pressure sensor 208 located along the dialysate line 216 connecting the dialyzer 110 to the equalizing chamber 210 is adapted to measure the pressure of the spent dialysate exiting the dialyzer 110. Any of various different types of pressure sensors capable of measuring the pressure of the spent dialysate passing from the dialyzer 110 to the equalizing chamber 210 can be used.

The spent dialysate collects in the equalizing chamber 210. The dialysate pump 212 is configured to pump the spent dialysate from the equalizing chamber 210 to the first chamber half 218 of the balancing device 206. As the first chamber half 218 of the balancing device 206 fills with the spent dialysate, fresh dialysate within the second chamber half 220 is expelled toward dialyzer 110. Subsequently, as the second chamber half 220 is refilled with fresh dialysate, the spent dialysate within the first chamber half 218 is forced through the drain line 128 to the drain.

The ultrafiltration line 129 is connected to an outlet of the equalizing chamber 210. The ultrafiltration pump 214 is operatively connected to the ultrafiltration line 129 such that when the ultrafiltration pump 214 is operated, spent dialysate can be pulled from the equalizing chamber 210 and directed to the drain via the ultrafiltration line 129. Operation of the ultrafiltration pump 214 while simultaneously operating the dialysate pump 212 causes increased vacuum pressure within the dialysate line 216 connecting the equalizing chamber 210 to the dialyzer 110, and thus creates increased vacuum pressure within the dialyzer 110. As a result of this increased vacuum pressure, additional fluid is pulled from the blood circuit into the dialysate circuit across the semi-permeable structure (e.g., semi-permeable membrane or semi-permeable microtubes) of the dialyzer 110.

As will be described in greater detail below, during treatment, dialysate is passed through the dialyzer while a patient's blood is passed through the blood circuit. By doing so, toxins migrate across the dialyzer membrane from the blood to the dialysate. This cleanses the patient's blood.

A method of preparing a patient for hemodialysis treatment will now be described.

Figure 6:
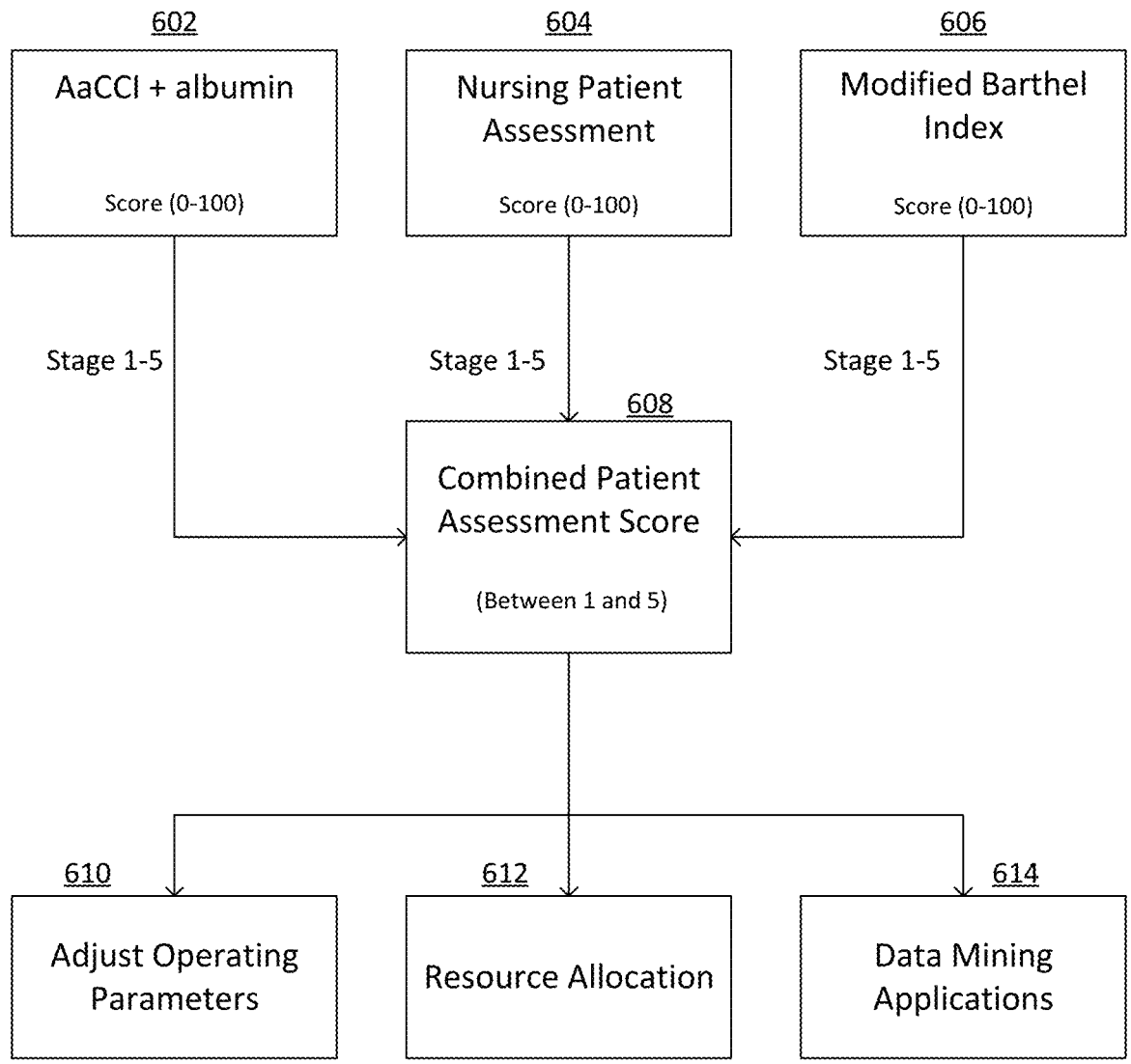
FIG. 6 is a block diagram showing patient assessments that are used to determine a Combined Patient Assessment Score for a patient who is to receive dialysis treatment.

A patient arrives at a medical facility for an initial hemodialysis treatment. Before the patient receives hemodialysis treatment, he or she undergoes a series of assessments by an appropriate caregiver (e.g., a doctor, nurse, medical assistant, secretary, etc.). Referring to FIG. 6, the patient undergoes three assessments: i) an Age adjusted Charlson Comorbidity Index (AaCCI) assessment that is adjusted based on an albumin measurement 602, ii) a Nursing Patient Assessment 604, and iii) a Modified Barthel Index assessment 606. As will be described below, this information can be used to determine a Combined Patient Assessment Score, which can, for example, be used to adjust various operating parameters of the hemodialysis machine, allocate resources, and detect treatment trends in data mining applications.

The Age adjusted Charlson Comorbidity Index assessment is adjusted based on an albumin measurement (AaCCI+albumin assessment). AaCCI is an indication of the patient's probability of survival over a given time period. AaCCI is based on a number and severity of 19 pre-defined comorbidity conditions that the patient possesses. Each comorbidity condition has a point value. Myocardial Infarction, congestive heart failure, peripheral disease, cerebrovascular disease, dementia, chronic pulmonary disease, connective tissue disease, peptic ulcer disease, mild liver disease, and diabetes without end-organ damage each has a point value of 1. Hemiplegia, moderate or severe renal disease, diabetes with end-organ damage, a tumor without metastasis (within the last 5 years), leukemia, and lymphoma each has a point value of 2. Moderate or severe liver disease has a point value of 3. Metastatic solid tumor and AIDS each has a point value of 6. The point values of the comorbidity conditions that the patient possesses are added up, resulting in a Charlson Comorbidity Index (CCI). The CCI is adjusted based on the patient's age, resulting in the AaCCI. If the patient is between 0 and 49, no points are added to the CCI. If the patient is between 50 and 59 years of age, 1 point is added to the CCI. If the patient is between 60 and 69 years of age, 2 points are added to the CCI. If the patient is between 70 and 79 years of age, 3 points are added to the CCI. If the patient is between 80 and 89 years of age, 4 points are added to the CCI. If the patient is between 90 and 99 years of age, 5 points are added to the CCI. If the patient is over 100 years of age, 6 points are added to the CCI.

Before the patient receives the initial hemodialysis treatment, information related to the patient's comorbidities is entered into the clinical server 123 (shown in FIG. 1). For example, the caregiver asks the patient for his age and whether he possesses each of the comorbidities. The caregiver enters this information into a computer that is connected to the clinical server 123, and the clinical server 123 determines the patient's AaCCI. The AaCCI corresponds to the patient's probability of survival.

In addition to the AaCCI being determined, the caregiver measures the concentration of albumin in the patient's blood. The concentration of albumin in the blood is typically in the order of grams per deciliter of blood. The patient's albumin measurement is also entered into the clinical server 123. The patient's probability of survival can be refined based on the albumin measurement. An albumin measurement of less than 3.5 grams per deciliter results in the patient's probability of survival decreasing, and an albumin measurement of greater than or equal to 3.5 grams per deciliter results in the patient's probability of survival increasing.

The clinical server 123 computes patient's probability of surviving for one year based on the patient's AaCCI and albumin measurement. Referring to FIG. 7, if the patient has an AaCCI of three or less and an albumin measurement of less than 3.5 grams per deciliter, the patient's probability of surviving for one year is 87%. If the patient has an AaCCI of four or five and an albumin measurement of less than 3.5 grams per deciliter, the patient's probability of surviving for one year is 61%. If the patient has an AaCCI of six or seven and an albumin measurement of less than 3.5 grams per deciliter, the patient's probability of surviving for one year is 49%. If the patient has an AaCCI of eight or more and an albumin measurement of less than 3.5 grams per deciliter, the patient's probability of surviving for one year is 30%. If the patient has an AaCCI of three or less and an albumin measurement of greater than or equal to 3.5 grams per deciliter, the patient's probability of surviving for one year is 89%. If the patient has an AaCCI of four or five and an albumin measurement of greater than or equal to 3.5 grams per deciliter, the patient's probability of surviving for one year is 75%. If the patient has an AaCCI of six or seven and an albumin measurement of greater than or equal to 3.5 grams per deciliter, the patient's probability of surviving for one year is 67%. If the patient has an AaCCI of eight or more and an albumin measurement of greater than or equal to 3.5 grams per deciliter, the patient's probability of surviving for one year is 50%.

The clinical server 123 computes the AaCCI+albumin assessment score based on the patient's probability of surviving for one year. If the patient's probability of surviving for one year is 87%, the patient's AaCCI+albumin assessment score is 87. If the patient's probability of surviving for one year is 30%, the patient's AaCCI+albumin assessment score is 30.

The AaCCI+albumin assessment score can have a value between 0 and 100. The clinical server 123 designates the AaCCI+albumin assessment as stage 1, 2, 3, 4, or 5 based on the AaCCI+albumin assessment score. A score of 0 to 60 corresponds to stage 5; a score of 61 to 70 corresponds to stage 4; a score of 71 to 80 corresponds to stage 3; a score of 81 to 90 corresponds to stage 2; a score of 91 to 100 corresponds to stage 1. Stage 5 indicates that the patient has low mobility and high complexity, while stage 1 indicates that the patient has high mobility and low complexity.

The Modified Barthel Index is an indication of the patient's self-care and mobility that establishes the patient's degree of independence from the help of others. The Modified Barthel Index is based on the caregiver's assessment of a patient's abilities regarding a number of items. FIGS. 8a-8k show each item, the possible scores for each item, and a description that corresponds to each score. The items include chair/bed transfer ability (FIG. 8a), ambulation dependency (FIG. 8b), ambulation/wheelchair dependency (FIG. 8c), stair climbing ability (FIG. 8d), toilet transfer ability (FIG. 8e), bowel control (FIG. 80, bladder control (FIG. 8g), bathing ability (FIG. 8h), dressing ability (FIG. 8i), personal hygiene maintenance (grooming) (FIG. 8j), and feeding ability (FIG. 8k). Each item has a weight that represents the maximum score that can be received for that particular item. The weights of all of the items add up to 100.

Before the patient receives the initial hemodialysis treatment, the caregiver (e.g., an experienced caregiver, such as a head nurse or a nursing shift leader) gives the patient a score for each item based on guidelines associated with each item. For example, referring to FIG. 8h, the maximum score for the "bathing" item is 5. If the patient is totally dependent for bathing, he receives a score of 0. If the patient requires assistance with either transfer to shower/bath or with washing or drying, he receives a score of 3. If the patient can use a bathtub, a shower, or take a complete sponge bath without another person being present, he receives a score of 5. The caregiver asks the patient a series of questions and gives the patient a score for each item based on the answers to these questions. The caregiver's observation of the patient can also impact the patient's scores.

The caregiver enters the score for each item into a computer that is connected to the clinical server 123 (shown in FIG. 1). The clinical server 123 computes the Modified Barthel Index score by adding together the scores for each item. The Modified Barthel Index score can have a value between 0 and 100. The clinical server 123 designates the Modified Barthel Index assessment as stage 1, 2, 3, 4, or 5 based on the Modified Barthel Index score. A score of 0 to 60 corresponds to stage 5; a score of 61 to 70 corresponds to stage 4; a score of 71 to 80 corresponds to stage 3; a score of 81 to 90 corresponds to stage 2; a score of 91 to 100 corresponds to stage 1. Stage 5 indicates low mobility and high complexity, while stage 1 indicates high mobility and low complexity.

Once the patient has undergone the Age adjusted Charlson Comorbidity Index (AaCCI)+albumin assessment and the Modified Barthel Index assessment, he is almost ready to receive the initial hemodialysis treatment. A caregiver brings the patient to the hemodialysis machine 102 (Shown in FIG. 1). As part of preparing the patient for treatment, the caregiver gives the patient the Nursing Patient assessment. The Nursing Patient assessment is an indication of the needs, preferences, and abilities of the patient.

Figure 9:
FIG. 9 is a spreadsheet that is displayed on the touch screen of the hemodialysis machine of FIG. 1 that a caregiver fills out in order to perform the Nursing Patient assessment of FIG. 6.

FIG. 9 shows a spreadsheet 900 that the caregiver fills out in order to perform the Nursing Patient assessment. The Nursing Patient assessment is based on the caregiver's assessment of the patient's symptoms regarding a number of items listed on the spreadsheet 900. The items include gastro-intestinal symptoms, respiratory distress, pain, mobility, chronic interdialytic muscle cramps, skin color and integrity, oedema, vascular access, and changes in mental state.

Some of the items include a number of sub-items. The gastro-intestinal symptoms item includes the sub-items: loss of appetite, nausea, vomiting, diarrhea, and constipation. The pain item includes the sub-items: back pain, extremity pain, abdominal pain, headache, and chest pain. The mobility item includes the sub-items: dizziness, weakness, and no physical activity performed. The skin color and integrity item includes the sub-items: redness/rash, pale/cianotyc, inflammation/abscess, dry/cracked skin, and jaundiced. The oedema item includes the sub-items: facial oedema, peripheral oedema, and extended neck veins. The vascular access item includes the sub-items: redness/pain at exit site, pus/bleeding on the exit site, fever, signs of intra-luminal thrombosis, and catheter malposition. The changes in mental state item includes the sub-items: lethargy/sleeping/passive, depressed feeling, anxious/bizarre behavior, insomnia, and confusion/altered consciousness. The respiratory distress item and the chronic interdialytic muscle cramps item do not include sub-items.

Each item has a weight that represents the maximum score that can be received for that particular item. The weights of all items add up to 100. For the items that have sub-items, each sub-item has a weight. The weights of the sub-items of a particular item add up to the weight of the item.

The items and sub-items included in the Nursing Patient assessment, as well as their corresponding weights, were determined by a group of nurses. The nurses identified symptoms that are particularly impactful on a patient's needs, preferences, and abilities. Symptoms that have the greatest impact are more heavily weighted, while symptoms that have a lesser impact are less heavily weighted.

The patient starts off with a Nursing Patient assessment score of 100. The caregiver observes the patient and asks the patient a series of questions. Based on the caregiver's observation and the answers to the questions, the caregiver determines whether the patient exhibits symptoms that correspond to the items or sub-items. For each symptom that the patient has that corresponds to an item or sub-item, the weight of the item or sub-item is deducted from the patient's Nursing Patient assessment score. If the patient has no symptoms that correspond to the items and sub-items, he is given a score of 100.

Referring to FIGS. 1 and 9, before the patient receives hemodialysis treatment, the caregiver accesses the spreadsheet 900 via the touch screen 118 of the hemodialysis machine 102. The spreadsheet 900 resides on the clinical server 123, and is accessible by the hemodialysis machine 102 via the network 122. Using the touch screen 118 or the control panel 120, the caregiver checks the box next to each symptom that the patient exhibits signs of. As each box is checked, the weight of the item of sub-item that corresponds to the symptom is deducted from the patient's Nursing Patient assessment score. Once the caregiver is finished conducting the Nursing Patient assessment, the clinical server 123 computes the Nursing Patient assessment score. The Nursing Patient assessment score can have a value between 0 and 100. The clinical server 123 designates the Nursing Patient assessment as stage 1, 2, 3, 4, or 5 based on the Nursing Patient assessment score. A score of 0 to 60 corresponds to stage 5; a score of 61 to 70 corresponds to stage 4; a score of 71 to 80 corresponds to stage 3; a score of 81 to 90 corresponds to stage 2; a score of 91 to 100 corresponds to stage 1. Stage 5 indicates low mobility and high complexity, while stage 1 indicates high mobility and low complexity.

Referring to FIG. 6, once the patient has undergone the Age adjusted Charlson Comorbidity Index (AaCCI)+albumin assessment 602, the Nursing Patient assessment 604, and the Modified Barthel Index assessment 606, the clinical server 123 designates each of the assessments as stage 1, 2, 3, 4, or 5. The clinical server 123 averages the three stage designations together, resulting in a Combined Patient Assessment Score 608 that represents the patient's general condition. The Combined Patient Assessment Score 608 has a value between 1 and 5.

FIG. 10 shows a table that illustrates a patient's general condition classification based on the Combined Patient Assessment Score. A Combined Patient Assessment Score of 4.3 to 5 indicates a fully complex patient. A Combined Patient Assessment Score of 3.5 to 4.2 indicates a substantially complex patient. A Combined Patient Assessment Score of 2.7 to 3.4 indicates a moderately complex patient. A Combined Patient Assessment Score of 1.9 to 2.6 indicates a minimally complex patient. A Combined Patient Assessment Score of 1 to 1.8 indicates a fully independent patient.

The Combined Patient Assessment Score 608 can be used to adjust operating parameters 610 of the hemodialysis machine 102 and to allocate resources 612 in a hemodialysis treatment center, as described in more detail below. The Combined Patient Assessment Score 608 and the information related to the AaCCI+albumin assessment, the Modified Barthel Index assessment, and the Nursing Patient assessment can also be utilized in data mining applications 614, also described in more detail below.

The Combined Patient Assessment Score can be taken into account when allocating resources and workflows in a hemodialysis treatment center. For example, prior to the patient commencing hemodialysis treatment, the patient's Combined Patient Assessment Score is retrieved from the clinical server 123 via the network 122. A manager at the treatment center considers the patient's Combined Patient Assessment Score when assigning the patient to a particular nurse.

The Combined Patient Assessment Score typically indicates the level of difficulty involved in treating the patient. FIG. 11 shows tables that illustrate possible resource allocation based on Combined Patient Assessment Scores of various patients. Nurses may be assigned patients such that the average Combined Patient Assessment Score of each nurse's patients is approximately the same. In this example, the average Combined Patient Assessment Score of Nurse 1's patients is 3.1, the average Combined Patient Assessment Score of Nurse 2's patients is 3.2, the average Combined Patient Assessment Score of Nurse 3's patients is 3.1, and the average Combined Patient Assessment Score of Nurse 4's patients is 3.1. As such, the expected difficulty in dealing with these patients is evenly distributed.

FIG. 12 shows tables that illustrate another possible allocation of resources based on Combined Patient Assessment Scores of various patients. Nurses may be assigned patients such that more experienced nurses are assigned patients that have relatively higher Combined Patient Assessment Scores, and less experienced nurses are assigned patients that have relatively lower Combined Patient Assessment Scores. In this example, the average Combined Patient Assessment Score of Experienced Nurse 1's patients is 4.3, the average Combined Patient Assessment Score of Experienced Nurse 2's patients is 4.4, the average Combined Patient Assessment Score of New Nurse 1's patients is 2.3, and the average Combined Patient Assessment Score of New Nurse 2's patients is 2.4. As such, the two experienced nurses who are better suited for treating complex patients are assigned relatively more complex patients than those assigned to the two new nurses.

Once the patient has been assigned to a caregiver and is about to commence hemodialysis treatment, the hemodialysis machine 102 retrieves the patient's Combined Patient Assessment Score from the clinical server 123 via the network 122. During treatment, the hemodialysis machine 102 may adjust various operating parameters based on the patient's Combined Patient Assessment Score.

A method of performing hemodialysis treatment will now be described

Referring to FIGS. 1 and 5, before hemodialysis treatment is initiated, saline is introduced from the saline bag 176 into the blood circuit via the saline delivery line 172 in order to prime the blood circuit. To draw the saline from the saline bag 176 into the blood circuit, a valve along the saline delivery line 172 is opened, a valve along the dialysate supply line 126 is closed, and the blood pump 132 is turned on. The saline enters the blood circuit via the pump line adaptor 158 (shown in FIGS. 2 and 3) and then flows through the U-shaped blood line 160 that engages the blood pump 132. The blood pump 132 forces the saline through the blood circuit toward the dialyzer 110. The saline flows through the dialyzer 110 and exits the dialyzer 110 via the dialyzer outlet line 170. As the saline flows through the dialyzer outlet line 170 toward the air release device 112, the saline passes through the venous pressure sensor capsule 156. Next, the saline flows through the entry port of the air release device 112 and fills the chamber of the air release device 112. To fill the chamber completely, the venous patient line 108, which leads away from the air release device 112, is clamped while the saline is forced into the chamber. Air is forced out the top of the chamber and through the vent assembly 114 as saline fills the chamber. The saline does not pass through the vent assembly because the membrane of the vent assembly 114 is hydrophobic.

After priming the blood circuit, the arterial and venous patient lines 106, 108 are connected to a patient 250, and hemodialysis is initiated. During hemodialysis, blood is circulated through the blood circuit (i.e., the various blood lines and blood components, including the dialyzer 110, of the blood component set 104). At the same time, dialysate is circulated through the dialysate circuit (i.e., the various dialysate lines and dialysate components, including the dialyzer 110).

Focusing first on the blood circuit shown on the left side of FIG. 5, during hemodialysis, the blood pump 132 is activated causing blood to circulate through the blood circuit. The blood follows the same basic route as the route of the saline described above and, for the most part, pushes the residual saline in the blood circuit through the various blood components and blood lines and back to the patient. The blood is drawn from the patient 250 via the arterial patient line 106 and flows to the arterial pressure sensor capsule 154. The arterial pressure sensor 184 on the front face of the module 130 (shown in FIG. 4) aligns with the pressure sensor capsule 154 and measures the pressure of the blood flowing through the blood circuit on the arterial side. The blood then flows through the U-shaped pump line 160, which is operatively engaged with the blood pump 132. From the pump line 160, the blood flows to the dialyzer 110. After exiting the dialyzer 110, the blood flows through the venous pressure sensor capsule 156 where the pressure of the blood on the venous side is measured by the associated pressure sensor 186 on the front face of the module 130 (shown in FIG. 4).

Upon measuring the pressure of the blood on the venous side, the hemodialysis machine 102 (shown in FIG. 1) may automatically adjust the blood flow rate. If, for example, the pressure of the blood on the venous side is less than or equal to 200 mmHg, the patient's Combined Patient Assessment Score is over 3.5, and symptoms of vascular access are present, the hemodialysis machine 102 adjusts the blood flow rate such that the pressure of the blood on the venous side rises to at least 200 mmHg. The processor 125 of the hemodialysis machine 102 sends an instruction to the blood pump 132 to adjust the blood flow rate accordingly, thereby reducing the risk of arteriovenous fistula/graft damage.

A Combined Patient Assessment Score of 3.5 or more indicates either a substantially complex patient or a fully complex patient. Such patients are more prone to issues during treatment and may require more frequent blood pressure monitoring. If the patient's Combined Patient Assessment Score is over 3.5, the hemodialysis machine 102 displays a notification on the touch screen 118 suggesting that the blood pressure monitoring rate by the Blood Pressure Monitor (BPM) (127 of FIG. 1) should be increased.

The notification includes one or more suggestions of appropriate blood pressure monitoring rates that can be used by the BPM 127. The suggested blood pressure monitoring rate may be at a particular interval. For example, the blood pressure of the patient may be measured every 5, 15, 30 or 60 minutes, to name a few. Alternatively, the blood pressure of the patient may be monitored more frequently (e.g., every 30 seconds) over a relatively short period (e.g., over a period of 5 minutes).

The blood pressure monitoring rate is not adjusted unless the caregiver accepts one of the suggestions. If the caregiver accepts one of the blood pressure monitoring rate suggestions, the processor 125 of the hemodialysis machine 102 sends instructions to the BPM 127 to monitor blood pressure at the accepted change in blood pressure monitoring rate.

Referring again to FIG. 5, in certain implementations, a drug, such as heparin, is injected into the blood via the drug delivery line 174 by activating the drug pump 192. Injecting heparin into the blood can help to prevent blood clots from forming within the blood circuit. Other types of drugs can alternatively or additionally be injected from the syringe 178 into the blood circuit. Examples of such drugs include vitamin D and iron supplements, such as Venofer® and Epogen®.

Next, the blood flows through the entry port of the air release device 112 in which any gas, such as air, in the blood can escape. When the blood enters the chamber of the air release device 112, the blood forces the saline at the bottom of the chamber, which remains in the chamber from the priming procedure, through the exit port of the air release device 112. However, the blood does not displace all of the saline within the chamber. Because of the size and shape of the chamber, the blood enters the chamber and only traverses part of the height of the chamber before flowing back down and exiting the exit port.

Any unbound gas, or air, that is in the blood, such as air that is introduced by the dialyzer 110 or syringe 178, rises as tiny air bubbles within the blood and saline until the air eventually vents out through the vent assembly 114.

After exiting the air release device 112, the blood travels through the venous patient line 108 and back to the patient.

During treatment, the caregiver continues to monitor the patient for symptoms that may arise. For example, the caregiver monitors the patient for the symptoms that corresponds to the items and sub-items of the Nursing Patient assessment. If the patient exhibits symptoms of changes in mental state (e.g., lethargy/sleeping/passive, depressed feeling, anxious/bizarre behavior, insomnia, and confusion/altered consciousness), the caregiver enters this information into the hemodialysis machine 102 using the touch screen 118. If the patient's Combined Patient Assessment Score is over 3.5, and the patient exhibits symptoms of changes in mental state, the hemodialysis machine 102 displays a notification on the touch screen 118 suggesting that VAM be employed. VAM is not employed unless the caregiver accepts the suggestion.

VAM is employed to provide early detection of an increased risk of venous needle dislodgement. When VAM is employed, the hemodialysis machine monitors sudden, small drops in blood pressure on the venous side (e.g., of approximately 15 mmHg). Even if the venous blood pressure does not fall below 200 mmHg from the sudden drop, an alarm condition is generated by an alarm management system based on a number of monitored signals related to the patient. The alarm management system considers variations to the patient's prior arterial and venous blood pressure measurements, as well as dynamic changes to the patient's arterial and venous blood pressure measurements. If an alarm condition occurs, the blood pump 132 is stopped and the venous occluder 190 is closed, thereby minimizing potential patient blood loss (e.g., to less than 200 mL).

Turning now to the dialysate circuit illustrated on the right side of FIG. 5, during hemodialysis, fresh dialysate is pumped into the dialysate circuit from the dialysate container 124 via the dialysate supply line 126 by running the dialysate pump 204. The fresh dialysate enters the second chamber half 220 of the balancing device 206. As spent dialysate enters the first chamber half 218 of the balancing device 206, the fresh dialysate is forced out of the second chamber half 220 and toward the dialyzer 110 via the dialysate line 216. The dialysate passes through the dialyzer 110 at the same time that the patient's blood is passed through the dialyzer 110 on an opposite side of the semipermeable structure of the dialyzer 110. As a result, toxins, such as urea, are transferred across a permeable structure (e.g., permeable membrane and/or permeable microtubes) of the dialyzer 110 from the patient's blood to the dialysate, and those toxins collect in the dialysate forming spent dialysate. The spent dialysate exiting the dialyzer 110 is circulated through the dialysate circuit to the equalizing chamber 210. The dialysate pump 212 draws spent dialysate from the equalizing chamber 210 and delivers it to the first chamber half 218 of the balancing device 206. As the spent dialysate fills the first chamber half 218, fresh dialysate within the second chamber have 220 is delivered to the dialyzer 110. As the second chamber half 220 is subsequently refilled with fresh dialysate, the spent dialysate within the first chamber half 218 is forced out of the balancing device 206 and into a drain via the drain line 128. The balancing device 206 balances the dialysate entering the dialysate circuit with the dialysate exiting the dialysate circuit to ensure that a substantially constant volume of dialysate remains within the dialysate circuit when ultrafiltration is not being performed.

In certain treatments, an ultrafiltration process is performed to remove excess fluid from the patient's blood. During ultrafiltration, a pressure gradient is created across the permeable structure between the dialysate side and the blood side of the dialyzer 110 by running the ultrafiltration pump 214. As a result, fluid is drawn across the semipermeable structure of the dialyzer 110 from the blood circuit to the dialysate circuit. Spent dialysate, including the toxins and excess fluid drawn from the patient, is drawn from the equalizing chamber 210 by the ultrafiltration pump 214 and is delivered to the drain via the ultrafiltration line 129.

In an attempt to maximize the efficiency of the dialysis treatment, it is beneficial for the hemodialysis machine 102 to employ the maximum ultrafiltration rate that the patient can safely handle. However, substantially or fully complex patients are more prone to issues during treatment and may not be capable of handling a relatively high ultrafiltration rate. Accordingly, the ultrafiltration rate can be adjusted based on the patient's Combined Patient Assessment Score. If the patient's Combined Patient Assessment Score is over 3.5, the hemodialysis machine 102 displays a notification on the touch screen 118 suggesting that the ultrafiltration rate should be decreased. The notification includes one or more suggestions of appropriate ultrafiltration rates that can be applied. The ultrafiltration rate is not adjusted unless the caregiver accepts one of the suggestions.

If the caregiver accepts one of the ultrafiltration rate suggestions, the processor 125 of the hemodialysis machine 102 sends an instruction to the ultrafiltration pump 214 to adjust its rate accordingly, thereby adjusting the pressure gradient that is created across the permeable structure between the dialysate side and the blood side of the dialyzer 110.

After completing the patient's treatment, the dialysate within the dialysate circuit is pumped to the drain using the dialysate pump 212 and/or the ultrafiltration pump 214. The blood component set 104 is then disconnected from the module 130 of the hemodialysis machine 102 and discarded, and the dialysate circuit is sterilized in preparation for a subsequent treatment.

The Age adjusted Charlson Comorbidity Index (AaCCI)+ albumin assessment score, the Modified Barthel Index score, and the Nursing Patient assessment score is recalculated at various times. The AaCCI portion of the AaCCI+albumin assessment is reperformed, and the AaCCI+albumin assessment score is recalculated, whenever the patient's comorbidities change or the patient's age would affect the AaCCI. The albumin measurement portion of the AaCCI+albumin assessment is reperformed, and the AaCCI+albumin assessment score is recalculated, every three months. The Modified Barthel Index assessment is reperformed, and the Modified Barthel Index score is recalculated, every three months or any time the patient's abilities change. The Nursing Patient assessment is reperformed, and the Nursing Patient assessment score is recalculated, before every dialysis treatment.

Each time one of these three scores is recalculated, the Combined Patient Assessment Score is recalculated. For example, after treatment, the patient may have a doctor's appointment with his primary care physician. The primary care physician may reperform the AaCCI portion of the AaCCI+albumin assessment for the patient. The primary care physician enters information related to the patient's comorbidities into a computer that is connected to the clinical server 123 (shown in FIG. 1). If the patient's comorbidities have changed, the clinical server 123 would recalculate the patient's AaCCI+albumin assessment score and also recalculate the patient's Combined Patient Assessment Score.

The next time the patient goes to a hemodialysis treatment center for treatment, the patient may receive another Modified Barthel Index assessment and another Nursing Patient assessment. Information related to these assessments may also be entered into the clinical server 123 in the manner described above, and the patient's Combined Patient Assessment Score is recalculated. The Combined Patient Assessment Score may then again be used to assign the patient to a particular nurse and to cause the hemodialysis machine 102 to adjust various operating parameters, as described above.

Historical data related to the AaCCI+albumin assessment scores, the Modified Barthel Index scores, the Nursing Patient assessment scores, and the Combined Patient Assessment Scores of patients can be stored by the clinical server 123. The clinical server 123 can evaluate and analyze the historical data of thousands of patients to detect treatment trends. The clinical server 123 may detect that patients having particular symptoms tend to receive a particular manual adjustment in their treatment (e.g., by caregivers administering hemodialysis on the patients). For example, the clinical server 123 may detect that in 95% of cases, when a patient exhibits symptoms of dizziness, the caregiver manually reduces the blood flow rate of the hemodialysis machine 102. As such, the clinical server 123 may propose automatically reducing the blood flow rate of the hemodialysis machine 102 whenever a patient's Nursing Patient assessment indicates that the patient exhibits symptoms of dizziness. In this way, the automatic operation of the hemodialysis machine 102 can be refined over time based on statistical data.

While certain implementations have been described, other implementations are possible.

While the information related to the patient's comorbidities has been described as being entered into a computer that is connected to the clinical server by the caregiver, the information related to the patient's comorbidities can be received by the clinical server in other ways. The patient may submit information related to his comorbidities to the clinical server himself before the dialysis treatment. In some implementations, information related to the patient's comorbidities has already been submitted to the clinical server by another caregiver, such as the patient's primary care physician. Similarly, the patient's albumin measurement can be performed by another caregiver separately from the dialysis treatment.

While the Age adjusted Charlson Comorbidity Index (AaCCI) and albumin measurement has been described as being used to compute the patient's probability of surviving for one year, the AaCCI and albumin measurement can be used to compute the patient's probability of surviving for various time periods. In some implementations, the AaCCI and albumin measurement is used to compute the patient's probability of surviving for two years.

While an albumin concentration of 3.5 grams per deciliter has been described as a threshold value that determines whether the patient's probability of survival based on the AaCCI is refined, other threshold values may be used by the clinical server, and other probabilities for survival may be computed by the clinical server instead of the probabilities shown in FIG. 7.

While the albumin measurement portion of the AaCCI+ albumin assessment has been described as being reperformed every three months, it can be reperformed at other frequencies.

While information related to the Modified Barthel Index assessment has been described as being entered into a computer that is connected to the clinical server by the caregiver, the information related to the patient's comorbidities can be received by the clinical server in other ways. In some implementations, information related to the patient's abilities has already been submitted to the clinical server by another caregiver, such as the patient's primary care physician.

While the Modified Barthel Index assessment has been described as being reperformed every three months, it can be reperformed at other frequencies.

While information related to the Nursing Patient assessment has been described as being entered into the touch screen of the hemodialysis machine by the caregiver, the information related to the Nursing Patient assessment can be received by the clinical server in other ways. In some implementations, the information related to the Nursing Patient assessment is entered into a computer that is connected to the clinical server by another caregiver.

While the Nursing Patient assessment has been described as being based on the patient's symptoms regarding particular items and sub-items, other items and sub-items can be included in the assessment. The weights of each item and sub-item can also be different from those shown in FIG. 9.

While the Nursing Patient assessment has been described as being reperformed before every dialysis treatment, it can be reperformed at other frequencies.

While the AaCCI+albumin assessment score, the Modified Barthel Index score, and the Nursing Patient assessment score have been described as having a value between 0 and 100, these scores can have other values. While the scores have been described as corresponding to particular stages for each assessment, the scores that correspond to particular stages can be different than those described above. Further, while each assessment has been described as being designated as stage 1, 2, 3, 4, 5, each assessment may have fewer or more stages.

While the Combined Patient Assessment Score has been described as being an average of the stage designations for the AaCCI+albumin assessment, the Nursing Patient assessment, and the Modified Barthel Index assessment, the Combined Patient Assessment Score can be calculated according to a different formula. In some implementations, one or more of the assessments is more heavily weighted than the other assessments.

While the Combined Patient Assessment Score has been described as having a value between 1 and 5, other values are possible.

While some of the adjustments to the hemodialysis machine based on the Combined Patient Assessment Score have been described as occurring automatically, these adjustments may alternatively require caregiver approval. Similarly, while some of the adjustments to the hemodialysis machine based on the Combined Patient Assessment Score have been described as requiring acceptance by a caregiver, these adjustments may alternatively occur automatically.

While the hemodialysis machine has been described as including certain specific features, any of various other types of hemodialysis machines can be used.

While the hemodialysis machine has been described as including a blood component set that includes various blood lines and blood components that are secured to a carrier body, in some implementations, various separate blood lines and blood components are independently secured to the hemodialysis machine. In certain implementations, the various blood lines and blood components are incorporated into an integrated cassette that can be secured to the hemodialysis machine.

While the hemodialysis machine has been described as including a touch screen, in some implementations, the hemodialysis machine includes a traditional monitor. In certain implementations, the hemodialysis machine includes a keyboard and/or a mouse that the caregiver can use to input information into the hemodialysis machine.

While the hemodialysis machine has been described as receiving fresh dialysate from a dialysate container, in some implementations, the hemodialysis machine makes its own dialysate by mixing water and other materials.

While the AaCCI+albumin assessment, the Nursing Patient assessment, and the Modified Barthel Index assessment have been described as being used in connection with a hemodialysis treatment, the patient assessments can be performed and the Combined Patient Assessment Score can be used for other kinds of medical treatments. The patient assessments and the Combined Patient Assessment Score can be used to adjust operating parameters of other medical treatment systems or allocate recourses in other medical contexts. Examples of other medical treatment systems with which the Combined Patient Assessment Score can be used include hemofiltration systems, hemodiafiltration systems, apheresis systems, cardiopulmonary bypass systems, and peritoneal dialysis systems.

A number of implementations of the invention have been described. Nevertheless, it will be understood that various modifications may be made without departing from the spirit and scope of the invention. Accordingly, other implementations are within the scope of the following claims.

What is claimed is:

1. A method comprising:
receiving patient assessment information concerning one or more subjective characteristics of a patient, the patient assessment information comprising a probability of the patient surviving for a particular length of time, and wherein the probability of the patient surviving for a particular length of time is based on an Age Adjusted Charlson Comorbidity Index and a concentration of albumin;
determining a patient assessment score based on the received patient assessment information, the patient assessment score corresponding to a likelihood of occurrence of an adverse physiological symptom;
modifying a continued operation of a medical fluid treatment machine based on the determined patient assessment score for preventing or reducing the likelihood of occurrence of the adverse physiological symptom, the modifying comprising adjusting at least one treatment parameter of the medical fluid treatment machine during the continued operation and while a treatment is provided by the medical fluid treatment machine to the patient, wherein adjusting the at least one treatment parameter includes adjusting a rate at which a blood pressure monitor of the medical fluid treatment machine monitors a blood pressure of the patient; and pumping medical fluid to and from the patient by the medical fluid treatment machine based at least in part on the modified continued operation of the medical fluid treatment machine.

2. The method of claim 1, wherein the at least one treatment parameter includes at least one of a blood flow rate, an ultrafiltration rate, and vascular access monitoring.

3. The method of claim 1, wherein modifying the continued operation of the medical fluid treatment machine comprises causing a message to be displayed that suggests an adjustment of the rate at which the blood pressure monitor of the medical fluid treatment machine monitors the blood pressure of the patient.

4. The method of claim 3, further comprising:
receiving an input in response to the message; and
upon receiving the input, adjusting the rate at which the blood pressure monitor of the medical fluid treatment machine monitors the blood pressure of the patient according to the suggestion.

5. The method of claim 1, wherein the patient assessment information further comprises one or more of:
information related to self-care and mobility of the patient; or
information related to needs, preferences, and abilities of the patient.

6. The method of claim 5, wherein the information related to the needs, preferences, and abilities of the patient includes information related to gastro-intestinal symptoms, respiratory distress, pain, mobility, chronic interdialytic muscle cramps, skin color and integrity, oedema, vascular access, and changes in mental state.

7. The method of claim 5, wherein the information related to the self-care and mobility of the patient includes information related to chair or bed transfer ability, ambulation dependency, wheelchair dependency, stair climbing ability, toilet transfer ability, bowel control, bladder control, bathing ability, dressing ability, personal hygiene maintenance ability, and feeding ability.

8. The method of claim 1, wherein the medical fluid treatment machine is a blood treatment machine.

9. The method of claim 1, wherein the medical fluid treatment machine is a dialysis machine.

10. The method of claim 9, wherein the dialysis machine is a hemodialysis machine.

11. The method of claim 9, wherein the dialysis machine is a peritoneal dialysis machine.

12. The method of claim 1, wherein the medical fluid is blood.

13. The method of claim 1, wherein the medical fluid is dialysate.

14. The method of claim 1, wherein:
the patient assessment information is received during a treatment provided by the medical fluid treatment machine, and
the patient assessment score is determined during the treatment provided by the medical fluid treatment machine.

15. The method of claim 1, wherein the patient assessment information includes at least one of an Age adjusted Charlson Comorbidity Index assessment, a Nursing Patient assessment, or a Modified Barthel Index assessment.

16. The method of claim 1, further comprising:
retrieving and analyzing historical data of a plurality of other patients, the historical data comprising, for each of the plurality of other patients, patient assessment information and at least one patient assessment score; and
identifying a treatment trend based on the analyzing;
wherein modifying the continued operation of the medical fluid treatment machine is further based on the identified treatment trend.

* * * * *